(12) United States Patent
Raz et al.

(10) Patent No.: US 6,291,234 B1
(45) Date of Patent: Sep. 18, 2001

(54) METHOD AND APPARATUS FOR TRANSFERRING A BIOLOGICAL SPECIMEN TO A CELLULAR SUSPENSION

(75) Inventors: Ryan S. Raz, Toronto; Zhaoyu Wang, Burnaby, both of (CA)

(73) Assignee: Morphometrix Technologies Inc., Toronto (CA)

( * ) Notice: Subject to any disclaimer, the term of this patent is extended or adjusted under 35 U.S.C. 154(b) by 0 days.

(21) Appl. No.: 09/382,607

(22) Filed: Aug. 25, 1999

Related U.S. Application Data

(60) Provisional application No. 60/097,844, filed on Aug. 25, 1998.

(51) Int. Cl.[7] .............................. C12M 1/24; C12Q 1/24
(52) U.S. Cl. ....................... 435/309.1; 435/30; 435/40.5; 435/307.1; 435/288.2; 600/570
(58) Field of Search .................. 435/40.5, 30, 288.1, 435/288.2, 304.1, 304.2, 307.1, 283.1, 309.1; 422/99, 102, 104; 600/569, 570, 572; 720/695, 697, 698, 702; 401/121, 122; 15/257.05, 257.01, 104.92, 142; 73/864.41

(56) References Cited

U.S. PATENT DOCUMENTS

| | | | |
|---|---|---|---|
| 830,763 | * | 9/1906 | Bradbury . |
| 835,131 | * | 11/1906 | Geer . |
| 857,975 | * | 6/1907 | Barrett . |
| 1,547,541 | * | 7/1925 | Wansner . |
| 1,735,756 | * | 11/1929 | Hart et al. . |
| 3,684,387 | * | 8/1972 | Glenn . |
| 4,403,624 | * | 9/1983 | Montgomery . |
| 4,657,869 | * | 4/1987 | Richards et al. . |
| 4,707,450 | * | 11/1987 | Nason . |
| 4,802,797 | * | 2/1989 | Cole . |
| 5,370,128 | * | 12/1994 | Wainwright . |
| 5,422,273 | * | 6/1995 | Garrison et al. . |

* cited by examiner

Primary Examiner—William H. Beisner
(74) Attorney, Agent, or Firm—Ridout & Maybee

(57) ABSTRACT

An apparatus and method for transferring exfoliated cells from a variety of specimen collection devices to a preservation fluid contained in a specimen vial. The apparatus comprises an interior frame member which is inserted into the specimen vial. The interior frame member includes a cross-bar member and an open-ended well. The cross-bar member includes a blade which provides an edge for scraping exfoliated cells from a spatula type specimen collection device. The cross-bar member also provides a lower edge for disconnecting a broom sampling head from a broom type collection device of disconnecting a combination type sampling head from a Combi™ type specimen collection device. The open-ended well comprises a sloped interior wall and a lower edge for removing exfoliated cells from a brush sampling head on a brush type collection device.

10 Claims, 7 Drawing Sheets

METHOD AND APPARATUS FOR TRANSFERRING A BIOLOGICAL SPECIMEN TO A CELLULAR SUSPENSION

This application claims the benefit of U.S. Provisional Application No. 60/097,844 filed Aug. 25, 1998.

FIELD OF THE INVENTION

The present invention relates to apparatus and method for transferring a biological specimen to a cellular suspension, and particularly to a method and apparatus for transferring exfoliated cells from a biological specimen collection exfoliation instrument to a cellular suspension in a specimen vial.

BACKGROUND OF THE INVENTION

In the field of medicine, pathology is the study of the symptoms of disease. One of the most important applications of pathology is the study of individual human cells collected from symptomatic or asymptomatic patients. This subject of pathology is commonly regarded to as cytopathology or simply cytology. Properly applied, cytology can provide valuable and often crucial evidence of the presence and progress of disease. The well-known Papanicolaou test, commonly referred to as the Pap test, is a good example of a cytopathology application. Under the Papanicolaou test, a careful assessment of epithelial cells exfoliated from the uterine cervix can provide advance warning of pre-invasive lesions, and a this early stage of detection anyone of a host of treatments is available to arrest the cancer with a high degree of success.

It is realized that the vehicle for these cytological evaluations plays an important role in the accuracy and precision of disease diagnosis. Until recently, the accepted collection standard for a Pap test was a conventional smear. The smear involved simply wiping exfoliated cells onto a glass microscope slide before fixation. The conventional smear suffered a number of drawbacks, and has now given way to more rigid techniques which are based in the fluid collection, presentation and preparation of epithelial cells.

Although the specific techniques known in the art for process epithelial cells for preparing cytological samples differ in various degrees, they all begin with the collection of epithelial cells in a suitable preservation fluid. It will be appreciated that the immediate transfer of exfoliated cells to the preservation fluid can eliminate preparation artifacts such as air-drying effects which tend to distort and alter the appearance of the cells. Furthermore, the preservation fluid provides a vehicle for carrying the epithelial cells in suspension for subsequent processing steps.

As fluid-based specimen collection and preservation techniques began to supplant the conventional smear for the Pap test, it was learned that the most important advantage in the new techniques lay in the recovery of the epithelial cells. Early published studies using flow cytometry established that transfer efficiency for a conventional smear was typically less than 10%. The new fluid-based specimen collection techniques were able to increase the rate of specimen recovery through the simple step of rinsing the exfoliation instrument, e.g. a plastic spatula or brush, in the preservation fluid. This was the principal reason for the increase in the diagnostic accuracy associated with early mono-layer specimens.

While it has been found that rinsing the exfoliation instrument in the preservation fluid provides an effective method for transferring epithelial cells to the preservation fluid (i.e., collection fluid), the technique is not entirely efficient and there is room for improvement. First, efficiencies may be found in improving the efficiency of the rinsing mode itself. Secondly, the sheer variety of exfoliation instruments commonly in use by today's clinicians has failed to lead to a simple efficient technique for transferring the exfoliated cells. The most common exfoliation instruments in use today include a "broom" instrument, an exfoliation instrument which is a combination of a spatula and a brush, and an instrument known as the Combi™ device which incorporates elements of both previous devices.

Since the conventional simple rinsing action cannot provide an effective transfer technique for all of the known exfoliation instruments, there still remains a need for a method or apparatus for efficiently transferring exfoliated cells from these instruments to the preservation fluid. Accordingly, there is a need for a generalized device for fluid-based sampling systems capable of handling the different types known exfoliation instruments.

BRIEF SUMMARY OF THE INVENTION

The present invention provides method and apparatus for efficiently transferring cells from a variety of common exfoliation instruments to a preservation or collection fluid for preparing a cytological specimen suitable for further processing and analysis.

In one aspect, the present invention provides an apparatus for transferring a biological specimen from a specimen collection device to a specimen vial having a mouth and containing a fluid for carrying the biological specimen, the apparatus comprising: (a) a side wall member being adapted for fitting into the specimen vial; (b) a cross-bar member, the cross-member being fixed to the side member and spanning a portion of the mouth of the specimen vial, the cross-member including an edge for removing the biological specimen from the specimen collection device and the biological specimen being contained by the fluid.

In another aspect, the present invention provides a method for removing a biological cells from a collection device having a broom sampling head comprising bristles attached to a shoulder member, the specimen collection system comprising a specimen vial filled with a preservation fluid, the specimen vial including an interior frame member the interior frame member having a cross-bar member, the cross-bar member spanning a portion of the mouth of the specimen vial and including a lower edge defining a gap between the bottom of the specimen vial, the method comprising the steps of: (a) inserting the broom sampling head of the collection device into the interior frame member in the specimen vial and below the level of preservation fluid; (b) pushing the sampling head of the collection device against the bottom of the specimen vial to splay the bristles and dislodge biological cells from the collection device; (c) rotating the collection device to lodge the shoulder member of the broom under the lower edge of the cross-bar member; (d) pulling upwards on the collection device to disconnect the broom sampling head from the collection device so that the broom sampling head remains submerged in the fluid contained in the specimen vial.

BRIEF DESCRIPTION OF THE DRAWINGS

Reference will now be made to the drawings which show, by way of example, preferred embodiments of the present invention, and in which.

DETAILED DESCRIPTION OF THE PREFERRED EMBODIMENTS

Figure 5A:
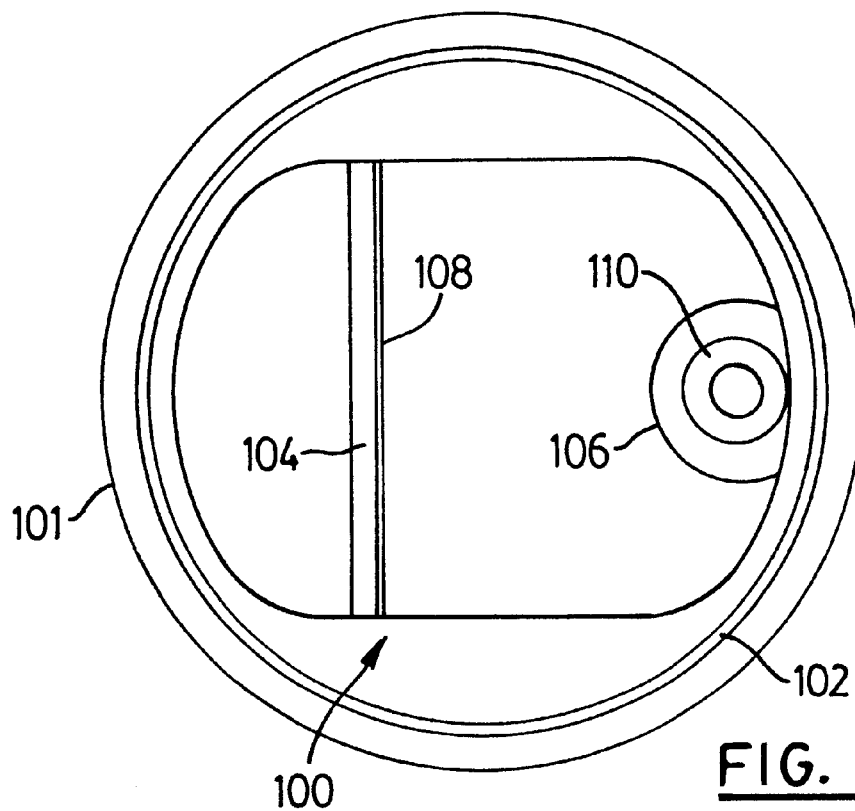
FIG. 5(a) is a top view showing a vial insert for transferring a biological specimen into a specimen vial according to the present invention.
Figure 5B:
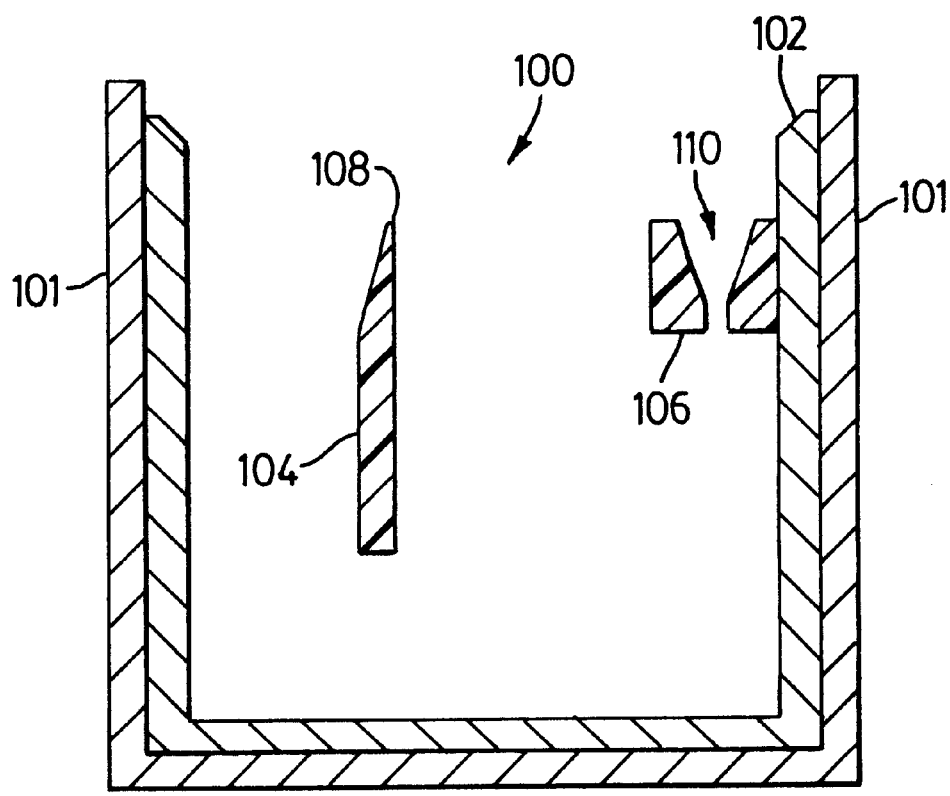
FIG. 5(b) is a cross-sectional view of the vial insert and specimen vial of FIG. 5(a)

As shown in FIGS. 5(a) and 5(b), the present invention comprises a vial insert 100 for transferring a biological specimen from an exfoliation device into a specimen vial 101. The specimen vial 101 comprises a conventional biological specimen container having an open top which is sealable. The specimen vial 101 is filled with a collection fluid which provides a suspension or transport for exfoliated cells. The vial insert 100 is mounted inside the specimen vial 101 and comprises circular wall 102, a cross-bar 104, and a well 106.

Referring to FIGS. 5(a) and 5(b), the circular wall 102 for the vial insert 100 is dimensioned to fit snugly inside the specimen vial 101. The cross-bar 104 spans the opening of the vial insert 100 and includes a blade portion 108. The blade 108 has a generally wedge-shape and provides an edge for removing cells from the exfoliation device as will be described below. The well 106 is fixed to the interior of the circular wall 102 and includes a conical opening 110. The conical opening 110 provides another surface for removing cells from the exfoliation device as will also be described below. As also shown in FIG. 5(a), the vial insert 100 has a oval arrangement which increases the effectiveness of subsequent dis-aggregation steps.

The vial insert 100 provides a mechanism for removing and transferring cells from an exfoliation device into a specimen vial 101. According to the invention, the vial insert 100 is suitable for use with a variety of known exfoliation devices.

Figure 1:
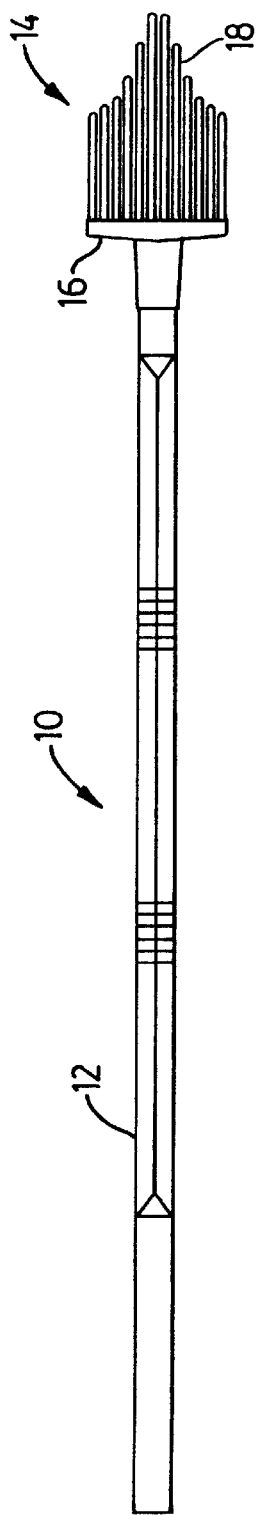
FIG. 1 shows a conventional broom exfoliation instrument.

Referring to FIG. 1, one type of exfoliation device 10 is known as the "broom" device. The broom exfoliation device 10 comprises a long handle 12 and a broom or brush 14. The broom 14 comprises a shoulder 16 with bristles 18 made from a soft plastic material and is attached to the handle 12 which is formed from a rigid plastic material. The broom device 10 is inserted into the cervical os of the patient and gently rotated under pressure. This causes a traumatic exfoliation of cervical epithelial cells from the ecto-cervix and the endo-cervical canal, preferably in the critical transformation zone for the patient. The exfoliated cervical cells are trapped on the bristles 18 of the broom 14 in a complex mass of cells and debris held together and to the bristles by mucus. As will be described below, the vial insert 100 provides an effective mechanism for removing the cells from the bristles 18 of the broom device 10 and into the collection fluid contained in the specimen vial 101.

Figure 2:
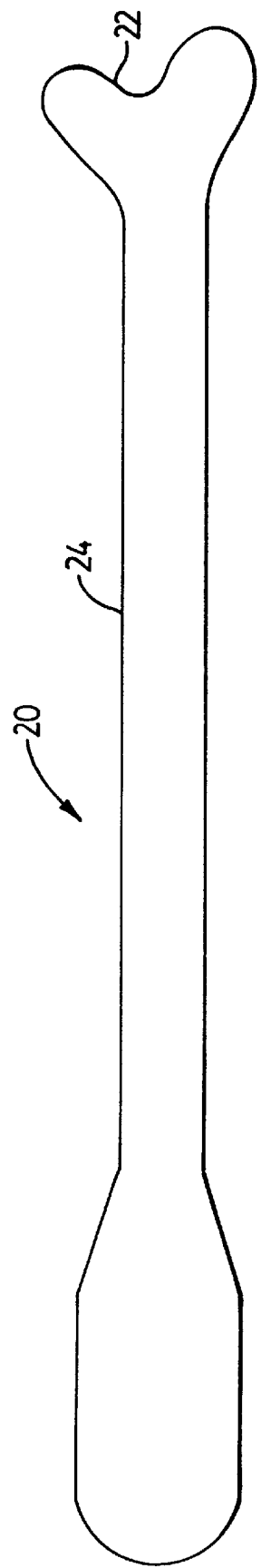
FIG. 2 shows a conventional spatula type exfoliation device.

The next type of known exfoliation device suitable for use with the vial insert 100 according to the present invention is a spatula device 20 as shown in FIG. 2. The spatula device 20 is typically formed from a rigid plastic material and comprises an end piece 22 and a longitudinal shaft 24. The end piece 22 and longitudinal shaft 24 are shaped to conform to the natural curvature of the cervix so that a cervical cell sample can be collected with a circular sweep of the spatula 20. The vial insert 100 provides an effective mechanism for removing the cervical cells from the spatuls 20 as will be described below.

Figure 3:
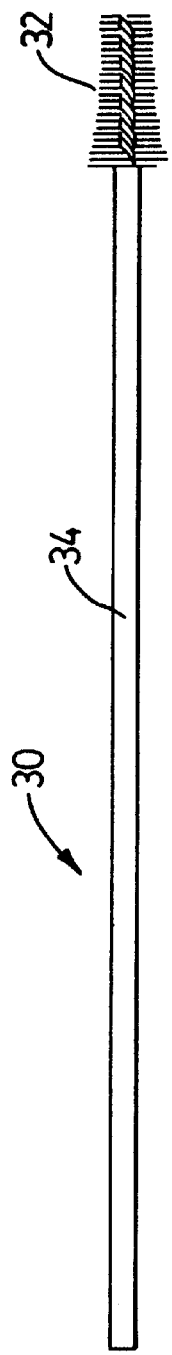
FIG. 3 shows a conventional brush type exfoliation device.

Another type of known exfoliation device suitable for use with the vial insert 100 is an endo-cervical brush device 30 as shown in FIG. 3. As shown in FIG. 3, the endo-cervical brush device 30 is a known instrument and comprises small plastic bristles 32 which are attached to a long plastic handle 34. The endo-cervical brush 30 is designed to be inserted into the cervical os and manipulated so that the abrasive action of the bristles 32 the glandular cervical cells and other cells are drawn onto the bristles 32. Again, the vial insert 100 provides a mechanism for also effectively removing exfoliated cells from the endo-cervical type brush 30.

Figure 4:
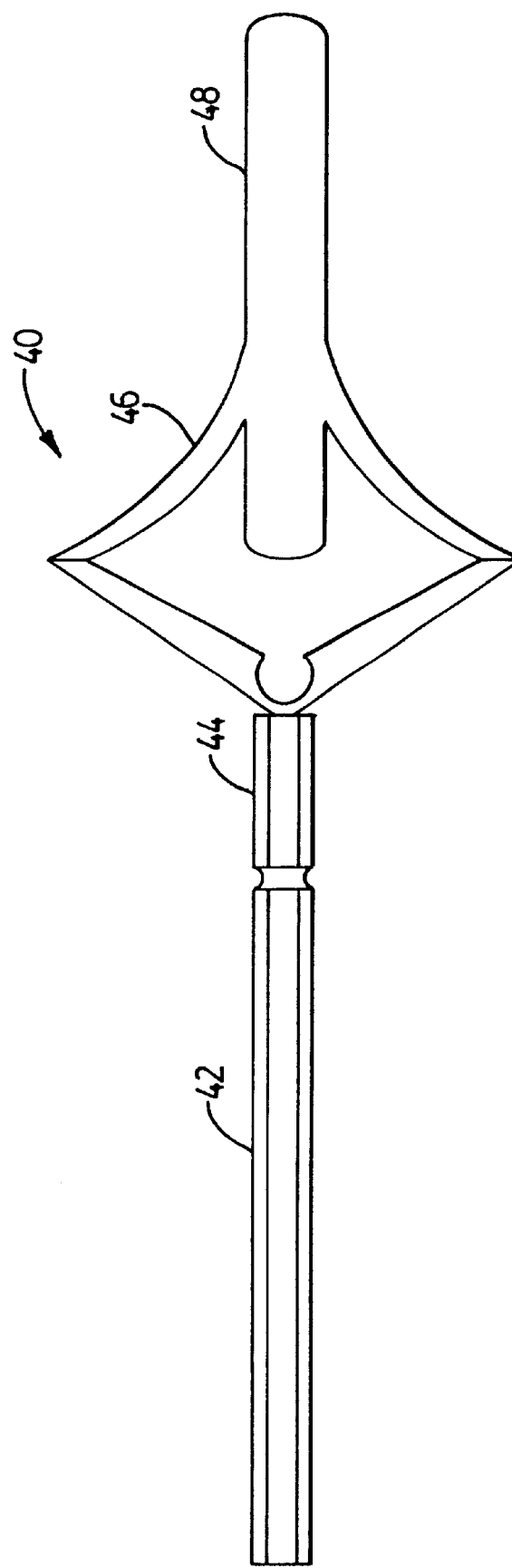
FIG. 4 shows a known combination or Combi™ exfoliation device.

The vial insert 100 according to the present invention is also suitable for used with the well-known combination or Combi™ exfoliation device 40 as shown in FIG. 4. The Combi™ exfoliation device 40 is a relatively new sampling device in the art. The device 40 is engineered to flex and conform to the cervical os and the surrounding region so that the transformation zone of the uterine cervix is completely covered by the exfoliating action of the device 40.

As shown in FIG. 4, the Combi™ exfoliation device 40 comprises a handle 42 which includes a mechanical break-joint 44. A flexible armature 46 attaches to the mechanical break-joint 44 and a sampling head 48 is attached to the flexible armature 46. The mechanical break-joint 44 allows the head 48 to be detached from the handle 42. The sampling head 48 is the active portion of the device 40 and is covered with a soft and abrasive micro-fiber bristle. The micro-fiber bristle on the sampling head 48 enhances removal of cervical cells both endo-cervically and exo-cervically. Pressure is exerted by the handle 42 which bears on the flexible armature 46.

After gathering the biological specimen using the Combi™ type exfoliation device 40, the specimen is generally transferred to a conventional Pap smear slide utilizing a rolling action. However, for fluid-based collection procedures, the problem remains of removing the cervical cells from the device 40 and placing them into suspension in a collection fluid contained in a specimen vial.

Reference is next made to FIGS. 6(a) to 6(d) which show the steps for transferring a biological specimen from the broom type exfoliation device 10 (FIG. 1) utilizing the vial insert 100 according to the invention. In FIGS. 6(a) to 6(d), the upper portion of the drawings shows a top view of the vial insert 100 and the lower portion shows a sectional view of the vial insert 100. For the broom type exfoliation device 10, the objectives of specimen transfer technique utilizing the vial insert 100 are two-fold. First, the bristles 18 on the broom 14 should be spread out to provide the greatest possible contact between the collection fluid and the exfoliated cells adhering to the bristles. Second, the broom 14 should be separated from the handle 12 to allow the broom 14 (i.e. bristles 18) to remain in the collection fluid thereby allowing specimen transfer to continue until the time the mono-layer specimen is to be prepared.

Figure 6D:
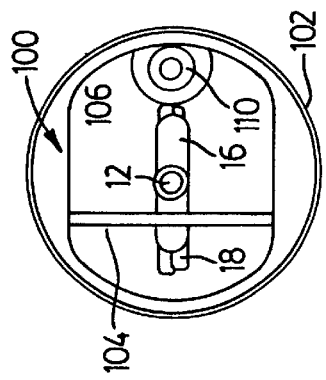
FIGS. 6(a) to 6(d) show in diagrammatic form the steps for transferring a biological specimen from a broom type exfoliation device (FIG. 1) utilizing the vial insert according to the invention.
Figure 6D:
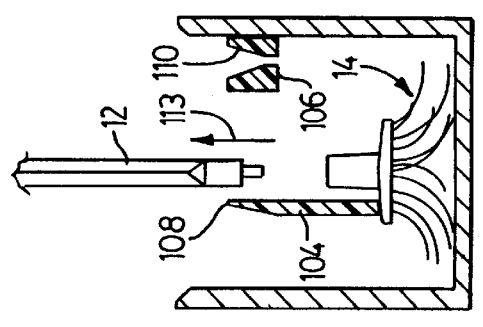
Figure 6C:
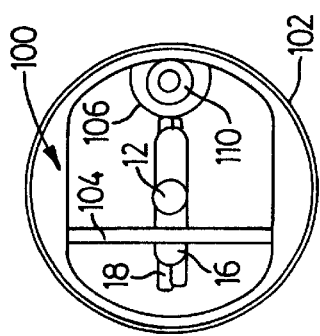
Figure 6C:
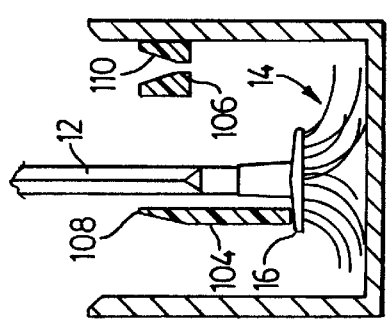
Figure 6B:
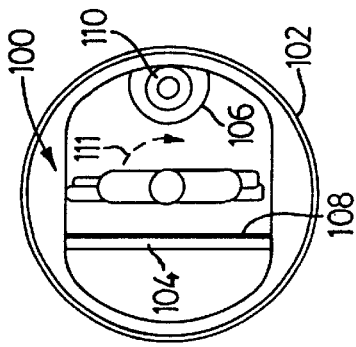
Figure 6B:
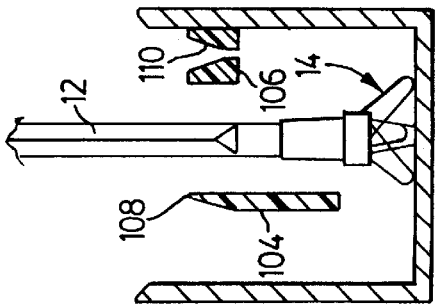
Figure 6A:
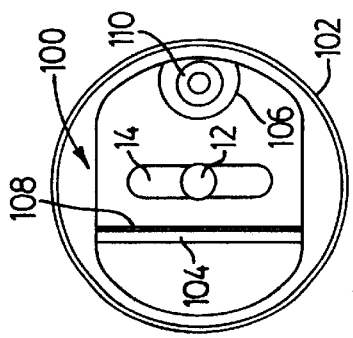
Figure 6A:
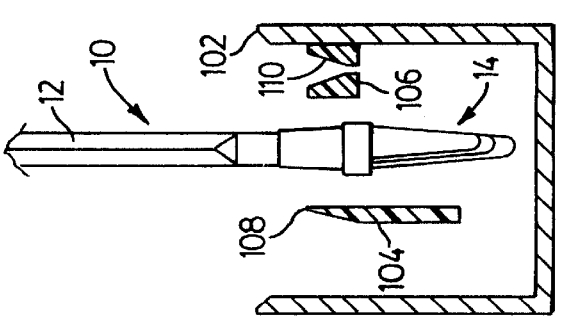

The first step shown in FIG. 6(a) involves inserting the exfoliation device 10 into the vial insert 100 and specimen vial 101. Preferably, contact with the crossbar 104 and well 106 is avoided when the device 10 is inserted into the collection vial 101. This is best accomplished by turning the device 10 as depicted in the upper portion of FIG. 6(a) so that the broom 14 is parallel to the crossbar 104.

The next step as shown in FIG. 6(b) involves pushing the broom 14 into the base of the vial 102 so that the bristles 18 are deflected and splayed outwardly. The splaying of the bristles 18 in the broom 14 starts the transfer of exfoliated cells from the bristles 18. The broom 14 is driven further into the bottom of the vial 101 and the handle 12 is turned 90° (as indicated by arrow 111). This results in the broom 14, specifically the shoulder 16, being wedged under the cross-bar 104 and the bristles 18 being splayed out as shown in FIG. 6(c).

The final step shown in FIG. 6(d) involves pulling the handle 12 upwards, i.e. in the direction of arrow 113. The upward movement disconnects the handle 12 from the broom 14 and the broom 14 remains in the specimen vial 101 lodged underneath the cross-bar 104 with the bristles 18 splayed in the collection fluid as depicted in FIG. 6(d).

Figure 7A:
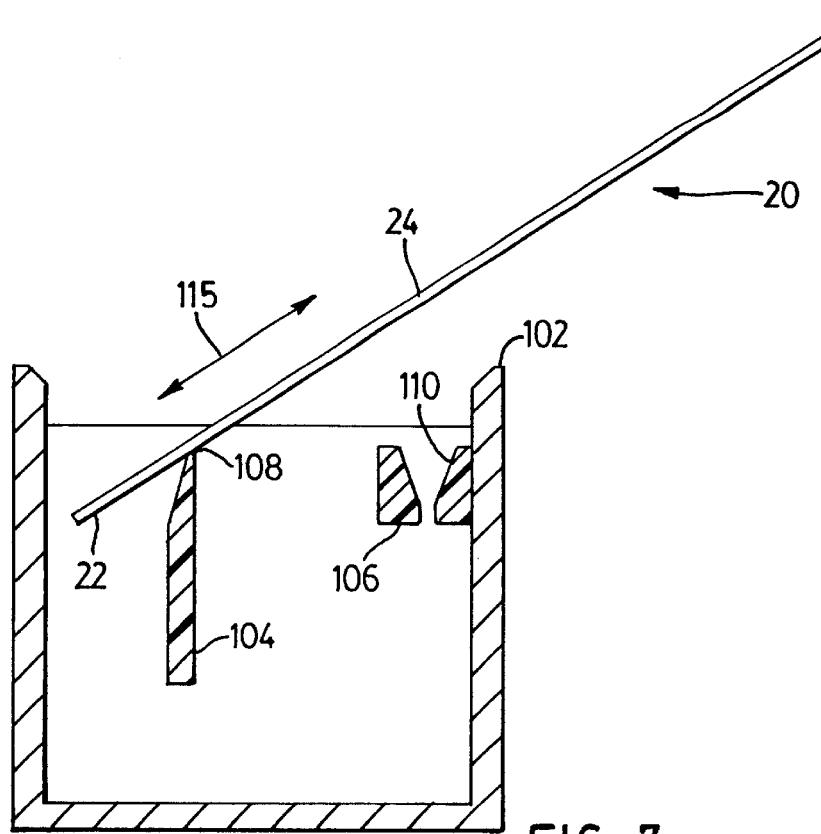
FIGS. 7(a) to 7(b) show in diagrammatic form the steps for transferring a biological specimen from a spatula type exfoliation device (FIG. 2) utilizing the vial insert according to the invention.
Figure 7B:
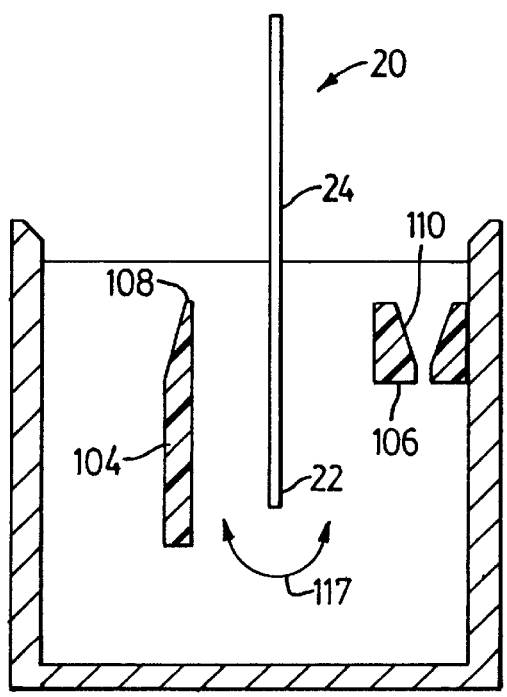

Reference is next made to FIGS. 7(a) to 7(b) which show the steps for transferring a biological specimen from the spatula type exfoliation device 20 (FIG. 2) utilizing the vial insert 100 according to the invention. The cells exfoliated by the spatula device 20 are effectively transferred to the collection fluid by utilizing the cross-bar 104 and specifically the blade portion 108. As shown in FIG. 7(a), the end 22 of the spatula device 20 is moved back and forth over the blade 108 as indicated by arrow 115. Since the blade 108 is below the level of the collection fluid, the cells scraped from the spatula 20 are transferred to the fluid. The scraping action is followed by a rinsing agitation movement (indicated by arrow 117) to transfer remaining exfoliated cells still adhering to the surface of the spatula device 20. The exfoliating cells removed from the device 20 remain in the collection fluid until the time to prepare the mono-layer specimen.

Figure 8:
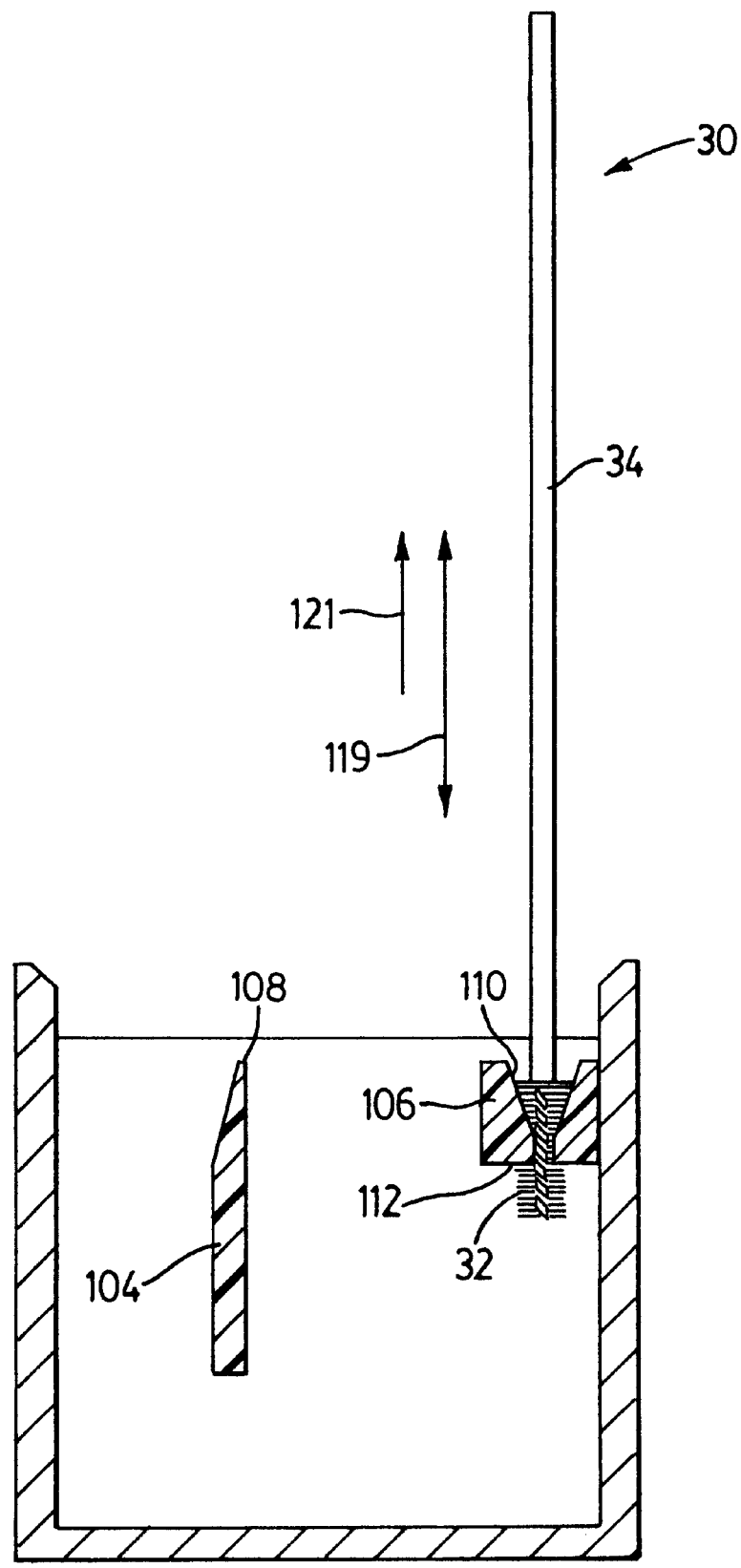
FIG. 8 shows in diagrammatic form the steps for transferring a biological specimen from a brush type exfoliation device (FIG. 3) utilizing the vial insert according to the invention.

Reference is next made to FIG. 8 which shows the steps for transferring a biological specimen from the endo-cervical brush type exfoliation device 30 (FIG. 3) utilizing the vial insert 100 according to the invention. The well component 106 of the vial insert 100 is intended for use with the endo-cervical exfoliation device 30. As shown in FIG. 8, the brush 32 of the endo-cervical exfoliation device 30 is inserted into the well 106. The conical opening 110 at its bottom end 112 is preferably only slightly larger than the wire core of the brush 32. As the endo-cervical brush 30 is pushed down in the direction of arrow 119, the cells adhering to the brush 32 are scraped off by the upper surfaces of the well opening 110. Withdrawing the exfoliation device 30 also causes cells to be dislodges from the brush 32 by the edge at the bottom end 112 of the well 110. Repeating this cycle a number of times results in the transfer of the vast majority of cells being separated from the endo-cervical brush 30 and suspended in the collection fluid.

Reference is next made to FIGS. 9(a) to 9(d) which show the steps for transferring a biological specimen from the Combi™ type exfoliation device 40 (FIG. 4) utilizing the vial insert 100 according to the invention. To effectively transfer exfoliated cells adhering to the Combi™ type device 40 the sampling head 48 should be immersed and kept in the collection fluid contained in the specimen vial 102. The vial insert 100 allows this to be accomplished effectively. As will now be described, the vial insert 100 provides a means for locking or bracing the Combi™ exfoliation device 40 so that a simple levering action can be used to separate the sampling head 48 from the handle 42.

Figure 9A:
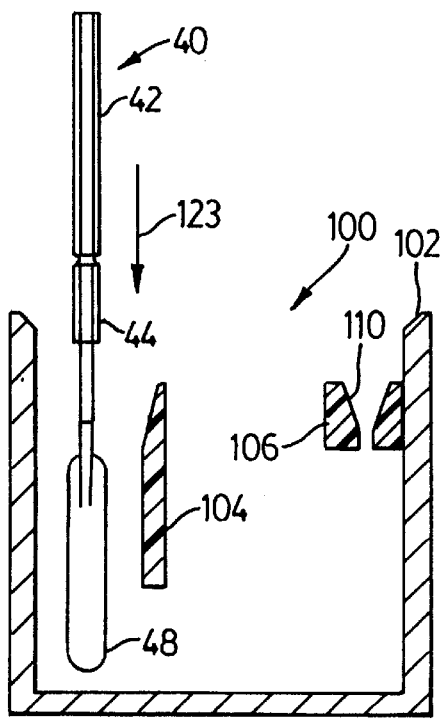
FIGS. 9(a) to 9(d) show in diagrammatic form the steps for transferring a biological specimen from a combination type exfoliation device (FIG. 4) utilizing the vial insert according to the invention.
Figure 9B:
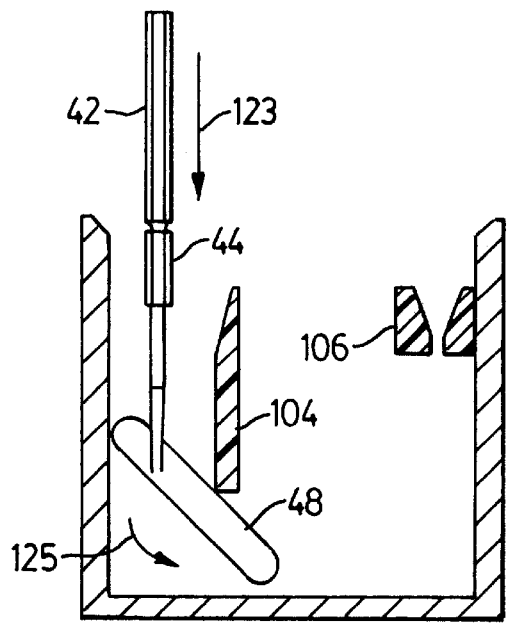
Figure 9C:
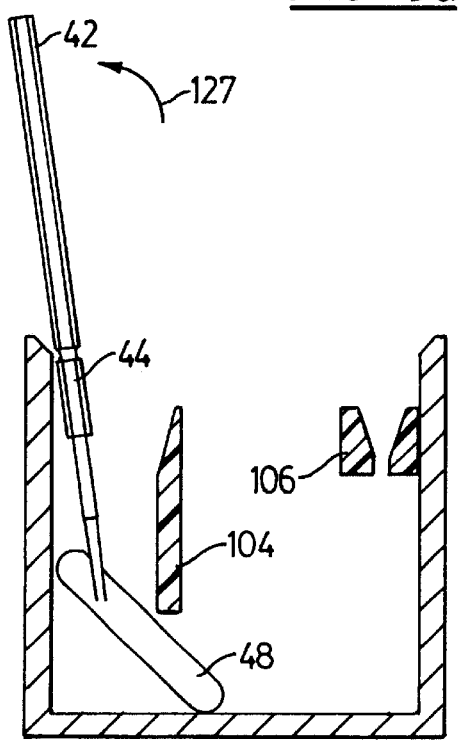
Figure 9D:
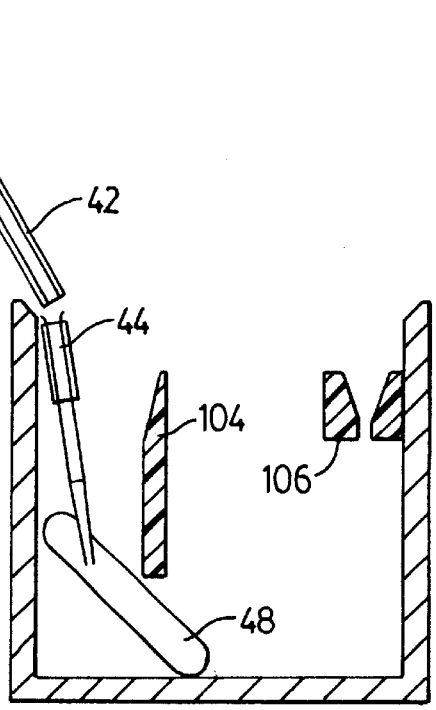

The first step as shown in FIG. 9(a) involves inserting the Combi™ type device 40 in the short side of the vial insert 100, i.e. between the cross-bar 104 and the side wall 102. Next the Combi™ device 40 is pushed down in the direction of arrow and the contact between the sampling head 48 and the bottom of the specimen vial 101 causes the sampling head 48 to turn (in the direction of arrow 125) and wedge under the cross-bar 104 as shown in FIG. 9(b). With the sampling head 48 firmly wedged under the cross-bar 104 and held in place, the handle 42 is broken at the break-away joint 44 by levering the handle 42 against the top edge of the specimen vial 101 in the direction of arrow 127 as shown in FIG. 9(c). As shown in FIG. 9(d), the handle 42 breaks away (arrow 129), leaving the sampling head 48 with the exfoliated cells submersed in the collection fluid in the specimen vial 101.

Advantageously, the vial insert 100 increases the rate of specimen recovery over a conventional fluid rinse technique. Additionally, the vial insert 100 provides a versatile single arrangement which supports a range of prevailing exfoliation devices. The vial insert 100 arrangement does not require further instruments and is useable by a single technician with minimal training.

The present invention may be embodied in other specific forms without departing from the spirit or essential characteristics thereof. Therefore, the presently discussed embodiments are considered to be illustrative and not restrictive, the scope of the invention being indicated by the appended claims rather than the foregoing description, and all changes which come within the meaning and range of equivalency of the claims are therefore intended to be embraced therein.

What is claimed is:

1. An apparatus for transferring a biological specimen from a specimen collection device to a specimen vial having a mouth and containing a fluid for carrying the biological specimen, said apparatus comprising:

(a) the side wall member being adapted for fitting into the specimen vial;

(b) a cross-bar member, said cross-bar member being fixed to said side wall member and spanning a portion of the mouth of the specimen vial, said cross-bar member including an edge for removing the biological specimen from the specimen collection device, and the biological specimen removed from the specimen collection device being contained by the fluid.

2. The apparatus as claimed in claim 1, wherein said cross-bar member includes a lower edge, said edge being located above the bottom of the specimen vial and defining a slot for engaging the sample end of the specimen collection device.

3. The apparatus as claimed in claim 1, further including an open-ended well for receiving a specimen collection device having a brush connected to the collection end of the device, said open-ended well being joined to said side wall member and including a lower edge for removing the biological specimen from the brush.

4. The apparatus as claimed in claim 3, wherein said open-ended well comprises an interior wall having a frustoconical shape.

5. An apparatus for transferring a biological specimen from a specimen collection device to a specimen vial having a mouth and containing a fluid for carrying the biological specimen, said apparatus comprising:

(a) a side wall member being adapted for fitting into the specimen vial;

(b) a cross-bar member, said cross-bar member being fixed to said side wall member and spanning a portion of the mouth of the specimen vial, said cross-bar member including a blade, said blade providing a scraping edge for removing the biological specimen from the specimen collection device;

(c) an open-ended well for receiving a specimen collection device having a brush connected to the collection end of the device, said open-ended well being connected to said side wall member including a lower edge, said lower edge providing a surface for removing the biological specimen from the brush; and (d) said biological specimen removed from the specimen collection device being suspended by the fluid.

6. A method for removing biological cells from a collection device in a specimen collection system, said collection device having a broom sampling head comprising bristles attached to a shoulder member, said specimen collection system comprising a specimen vial filled with a preservation fluid, said specimen vial including an interior frame member said interior frame member having a cross-bar member, said cross-bar member spanning a portion of the mouth of the specimen vial and including a lower edge defining a gap between the bottom of the specimen vial, said method comprising the steps of:

(a) inserting the broom sampling head of the collection device into the interior frame member in the specimen vial and below the level of preservation fluid;

(b) pushing the sampling head of the collection device against the bottom of the specimen vial to splay the bristles and dislodge biological cells from the collection device;

(c) rotating the collection device to lodge the shoulder member of the broom under the lower edge of the cross-bar member;

(d) pulling upwards on the collection device to disconnect the broom sampling head from the collection device so that the broom sampling head remains submerged in the fluid contained in the specimen vial.

7. A method for removing biological cells from a collection device in a specimen collection system, said collection device having a spatula sampling end, said specimen collection system comprising a specimen vial filled with preservation fluid, said specimen vial including an interior frame member said interior frame member having a cross-bar member, said cross-bar member spanning a portion of the mouth of the specimen vial and including a blade for providing a scraping edge for removing biological cells from the spatula sampling end, said method comprising the steps of:

(a) inserting the spatula sampling head of the collection device into the preservation fluid;

(b) scraping the spatula sampling head of the collection device against the blade edge of the cross-bar member to dislodge biological cells from the collection device.

8. The method as claimed as claim 7, further including the step of rinsing the spatula sampling head of the collection device to remove biological cells still adhering to the collection device.

9. A method for removing biological cells from a collection device in a specimen collection system, said collection device having a brush sampling head comprising bristles attached to a core member, said specimen collection system comprising a specimen vial filled with a preservation fluid, said specimen vial including an interior frame member said interior frame sampling head, said open-ended well for receiving the brush sampling head, said open-ended well being connected to said interior frame member and including a lower edge, said lower edge providing surface for removing the biological specimen from the brush, said method comprising the steps of:

(a) inserting the brush sampling head of the collection device into the open-ended well;

(b) moving the brush sampling head up and down through the open-ended well so as to press bristles forming the brush against the lower edge of the well to dislodge cells from the bristles.

10. A method for removing biological cells from a combination type collection device in a specimen collection system, said combination type collection device having a handle and a detachable sampling head connected to the handle and adapted for carrying biological cells, said specimen collection system comprising a specimen vial filled with preservation fluid, said specimen vial including a interior frame member said interior frame member having a cross-bar member, said cross-bar member spanning a portion of the mouth of the specimen vial and including a lower edge defining a gap between the bottom of the specimen vial, said method comprising the steps of:

(a) inserting the combination type collection device into the specimen vial between the cross-bar member and the interior frame member; into the specimen vial between the cross-bar member and the interior frame member;

(b) pushing the sampling head of the collection device against the bottom of the specimen vial and underneath the lower edge of the cross-bar member to lodge the sampling head of the collection device;

(c) pushing the handle of the collection device against a top edge of the interior frame member to disconnect the sampling head from the handle, so that the sampling head remains lodged underneath the cross-bar member and the specimen vial.

* * * * *